United States Patent [19]

Bulko et al.

[11] Patent Number: 5,195,790
[45] Date of Patent: Mar. 23, 1993

[54] APPARATUS FOR BLOCKING THE MOVEMENT OF A CHAMBER DOOR

[75] Inventors: John M. Bulko; Arthur T. Nagare, both of Erie, Pa.

[73] Assignee: American Sterilizer Company, Erie, Pa.

[21] Appl. No.: 868,804

[22] Filed: Apr. 15, 1992

[51] Int. Cl.$^5$ .............................................. E05C 3/26
[52] U.S. Cl. .................................. 292/201; 292/207; 49/449
[58] Field of Search ................ 292/201, 207, DIG. 60, 292/216; 49/449

[56] References Cited

U.S. PATENT DOCUMENTS

| | | | |
|---|---|---|---|
| 1,323,007 | 11/1919 | Brunette | 292/144 X |
| 1,821,491 | 9/1931 | Barrows | 49/370 X |
| 2,868,551 | 1/1959 | Avellone et al. | 292/304 X |
| 3,296,742 | 1/1967 | Mortimer | 292/201 X |
| 3,407,535 | 10/1968 | Purkey | 292/201 X |

*Primary Examiner*—Richard E. Moore
*Attorney, Agent, or Firm*—Jones, Day, Reavis & Pogue

[57] ABSTRACT

An apparatus is provided for preventing the opening of a chamber door of a sterilizer or an autoclave. The apparatus is used on sterilizer and autoclave door systems wherein the door is slidably attached to the chamber. However, the present invention may also be used to control other doors. The apparatus includes a cylinder and piston in fluid communication with the chamber which is actuated when the pressure within the chamber is above a threshold level. A cam, pivotally attached to the side guide bar of the sterilizer, cooperates with the piston to prevent movement of the cam with the piston in the extended position but to allow movement when the piston is retracted. A pin, mounted to the door, cooperates wiht the cam such that the pin must slide along the lobe surface of the cam in order for the door to open. When the piston is in the extended position, the cam cannot move and the pin is received in a recess in the cam surface. The cylinder and piston are mounted to accept a lateral force on the piston without damage to the piston or cylinder. An adjustable stop screw, mounted perpendicular to the piston, prevents movement of the piston beyond acceptable limits. The cylinder is mounted to a housing by bolts which have between the bolt head and the housing resilient washers which allow the cylinder to pivot slightly so that the piston is not damaged by the impact of the cam.

5 Claims, 7 Drawing Sheets

APPARATUS FOR BLOCKING THE MOVEMENT OF A CHAMBER DOOR

BACKGROUND OF THE INVENTION

1. Field of the Invention

The invention relates to apparatus for blocking the movement of a door, in particular, to apparatus for blocking the movement of a door on autoclave and sterilizer chambers while the chamber is pressurized.

2. Description of the Invention Background

Sterilizers and autoclaves are known in the art and are generally used in hospitals, industrial laboratories and other facilities for the purpose of sterilizing various solid, porous, and liquid articles. Typically, the sterilizer or autoclave chamber is located in a wall between a controlled environment room such as a laboratory or an operating room and an adjacent room wherein the strict environmental controls and parameters are not maintained.

Vertically sliding doors are typically used in connection with such machines because they require a minimum of space in relation to the size of the opening they provide and they do not interfere with the loading and unloading of the machine. Such vertically sliding doors can be controlled by motor-controlled cables which serve to move the door between open and closed positions or can be moved by manual operation. Sterilizers typically utilize high pressure steam for sterilization which presents a potential hazard to the operator. Specifically, if a sterilizer door is opened while the chamber is pressurized, there exists a risk of physical injury to the operator.

Thus, the need exists for an apparatus which will automatically prevent the opening of the chamber door when a threshold level of pressure exists in the chamber. The apparatus must be mechanically operated so that in the event of a power failure the blocking apparatus will operate.

SUMMARY OF THE INVENTION

The present invention comprises an apparatus, attached to a sterilizer, for preventing the opening of the door when the chamber is pressurized. The apparatus of the present invention is adapted to be used on sterilizer and autoclave door systems wherein the door is slidably attached to the end of the chamber. However, the present invention may also be used to block the movement of other doors and like members that require movement between different positions.

The present invention includes a cylinder and piston in fluid communication with the sterilizer chamber which is actuated when the pressure within the chamber is above a threshold level, such as, for example, 2 psi above atmospheric. A cam, pivotally attached to the guide member of the sterilizer, cooperates with the piston in such a manner as to prevent movement of the cam when the piston is in the extended position. A pin, mounted to the door, cooperates with the cam such that the pin must slide along the lobe surface of the cam in order for the door to open. When the piston is in the extended position, the cam cannot move and the pin is held captive in a recess in the cam surface and, thus, is blocked from moving. Therefore, since the pin is held captive, the door is prevented from opening when the piston is extended. When the piston is retracted, the cam is free to rotate and the pin is free to slide along the lobe surface. When the piston is retracted and the door is moving up from the open position, the pin moves along the lobe surface and rotates the cam which is free to move past the retracted piston. The apparatus operates without interfering with the door support, sealing hardware and movement of the door.

The cylinder and piston are mounted in such a manner as to accept a lateral force on the piston without damage to the piston or cylinder. An adjustable stop screw, mounted perpendicular to the piston, prevents movement of the piston beyond acceptable limits. Additionally, the cylinder is mounted to a housing by bolts which have, between the bolt head and the housing, resilient, force absorbing washers. Therefore, the piston and cylinder are able to pivot slightly (e.g. about 1 degree) so that the piston is not damaged by the impact of the cam.

One sterilizer which could be fitted with the blocking apparatus is disclosed in U.S. Patent Application Ser. No. 848,805, entitled "Apparatus For Eliminating Slack in Motorized Cables", the disclosure of which is incorporated herein by reference.

Accordingly, the present invention provides solutions to the aforementioned problems encountered when using a sterilizer or other pressure vessel. These and other details, objects and advantages of the invention will become apparent as the detailed description of the present invention proceeds.

BRIEF DESCRIPTION OF THE DRAWINGS

The preferred embodiment of the invention will now be described by way of example only, with reference to the accompanying Figures wherein like members bear like reference numerals and wherein.

DETAILED DESCRIPTION OF THE PREFERRED EMBODIMENT

Figure 1:
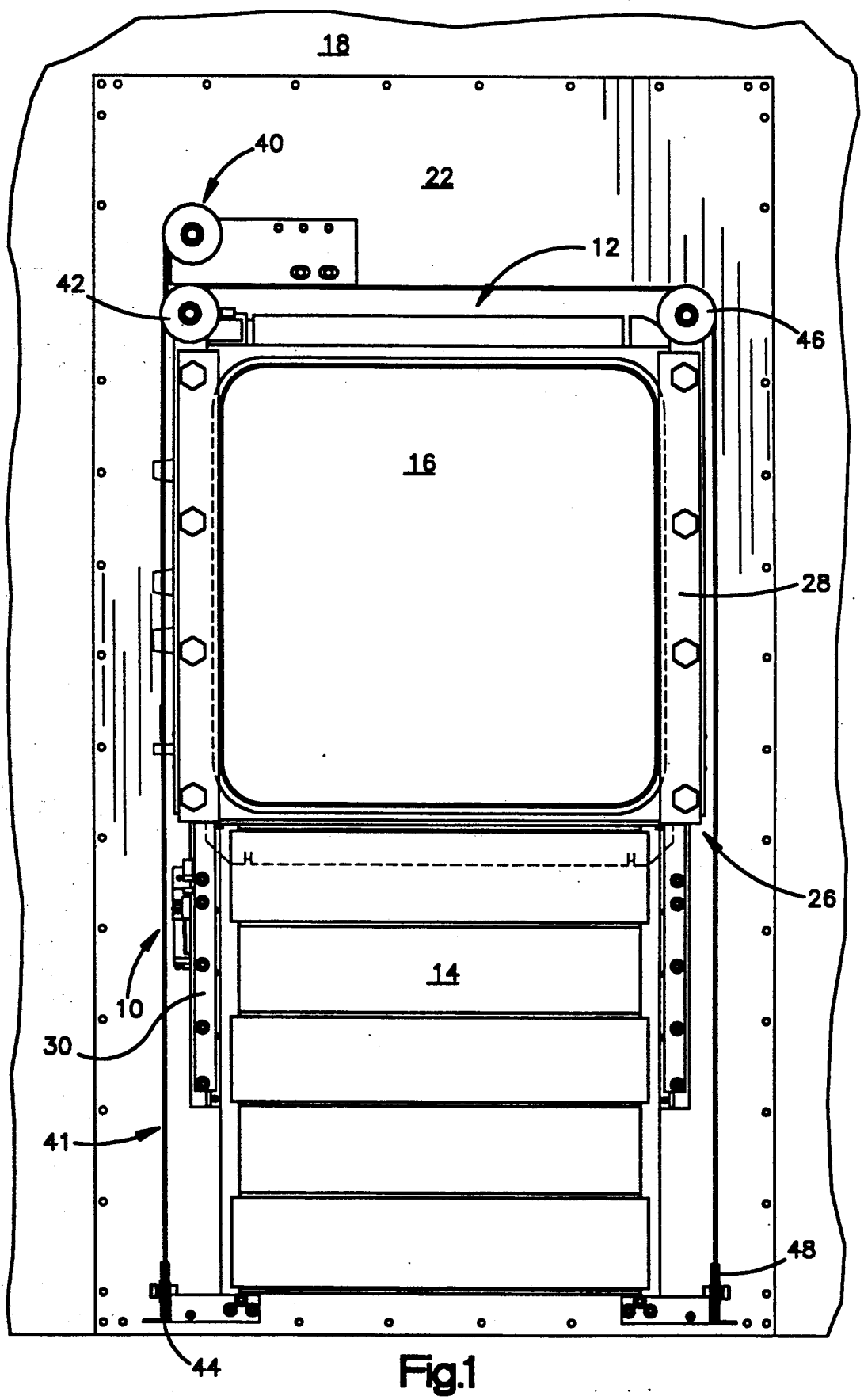
FIG. 1 is a front elevational view of a sterilizer and door with the door in the open position.

Referring now to the drawings which are for purposes of illustrating the preferred embodiment of the present invention only and not for purposes of limiting the same, the Figures show an apparatus generally designated as 10, adapted to prevent the opening of the door 14 of a conventional sterilizer 12. The skilled artisan will appreciate, however, that the present invention may be used to control other doors of similarly constructed chambers.

Figure 2:
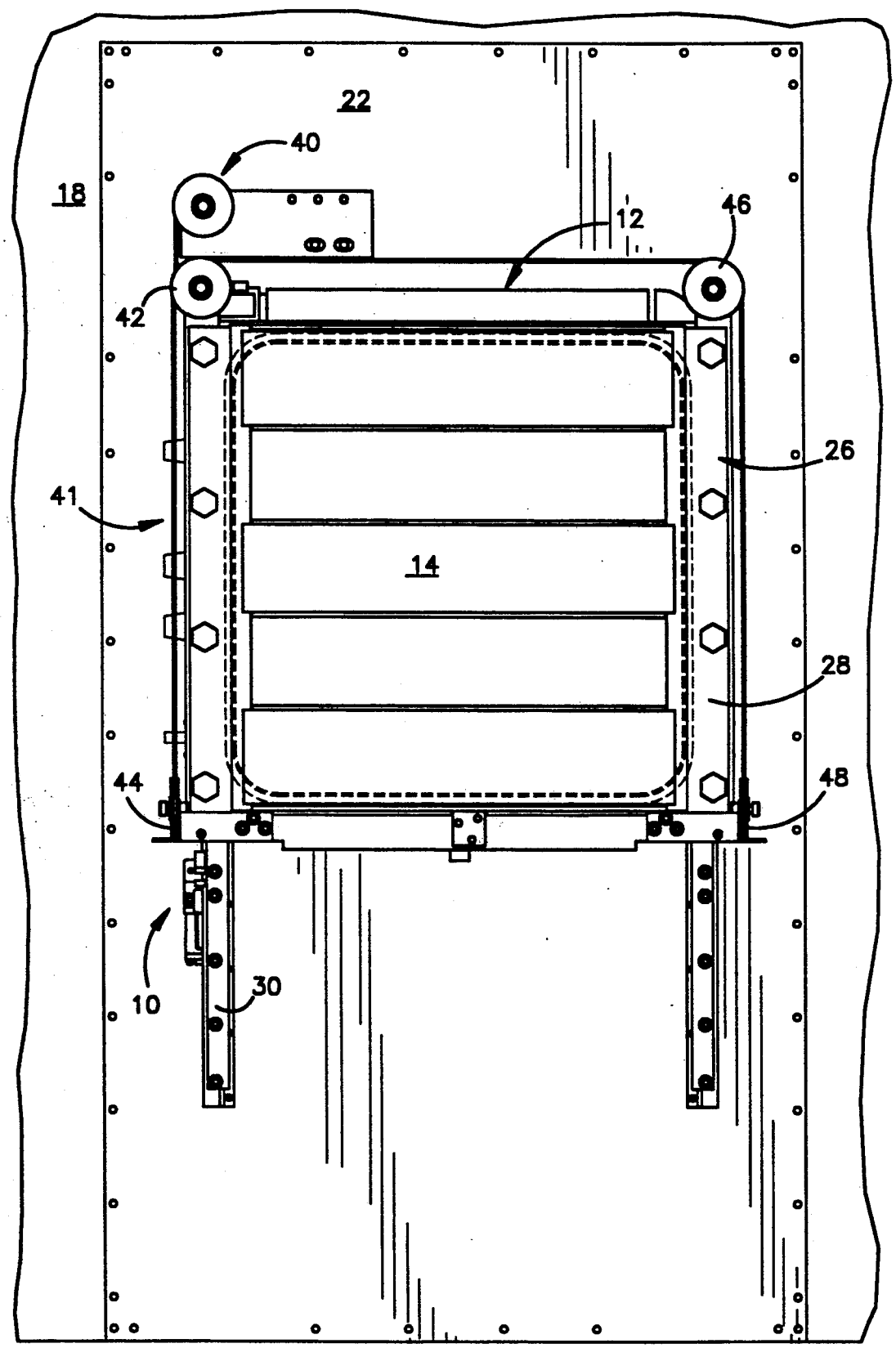
FIG. 2 is a front elevational view of a sterilizer and door with the door in the closed position.

More particularly and with reference to FIGS. 1 and 2, the sterilizer 12 is exemplary of typical sterilizers having vertically sliding doors, the construction and operation of which are known in the art. As such, a detailed description of the sterilizer 12 need not be set forth herein beyond that which is necessary to understand the present invention.

As particularly shown in FIG. 1, the sterilizer 12, having a vertically slidable door 14 attached thereto, is supported above the floor level by a stand member (not shown). The sterilizer 12 is typically located in a non-environmentally controlled room behind wall 18 and is arranged to be accessed from an adjacent environmentally controlled or "clean" room, such as, for example, a controlled laboratory environment. It will be appreciated, however, that the sterilizer 12 may also be equipped with a second access door (not shown) in its opposite end that may be accessed from the opposite side. It will be further appreciated that the present invention may also be installed on that end of the sterilizer to control the corresponding chamber door.

Figure 3:
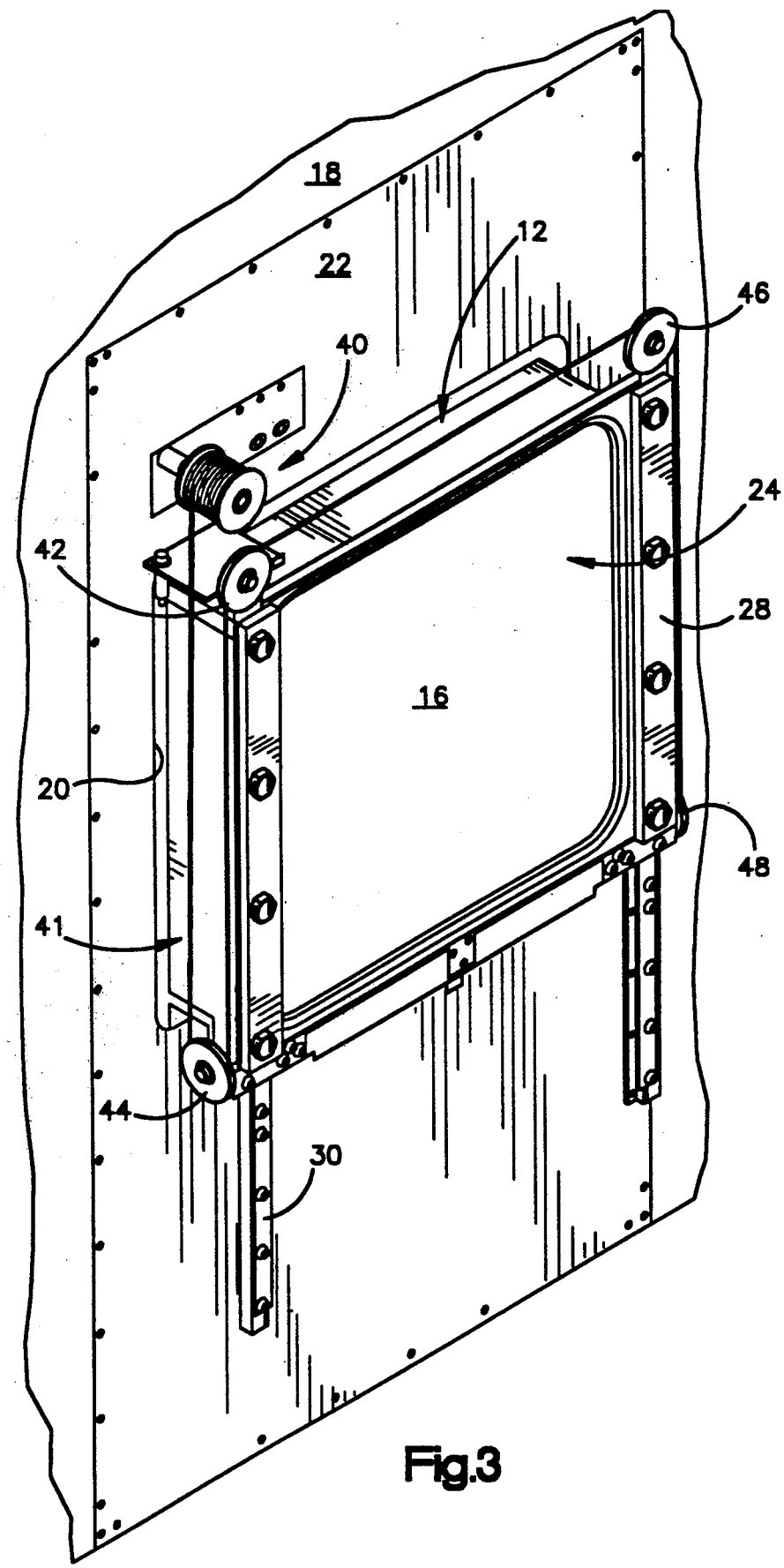
FIG. 3 is an isometric view of a sterilizer with the present invention and the door omitted.

Typically, the sterilizer 12 is arranged so that the opening 16 of the sterilizer chamber 24 and the door 14 are located within the clean room while the remainder of the sterilizer 12 is located in the adjacent "non-clean" room behind wall 18. A portion of the sterilizer 12 preferably extends through an opening 20 (FIG. 3) in the wall 18. A sealing flange 22, preferably fabricated from an elastomeric material, is located in the opening 20 and serves to provide an air tight seal around the sterilizer 12. The skilled artisan will appreciate that the sealing flange 22 may be fabricated from a variety of other materials such as, for example, steel or aluminum.

Referring now to FIGS. 1 and 2, the sterilizer door 14 is preferably slidably attached to the open end of the sterilizer 12 by door retainer hardware generally designated as 26. More specifically, the door retainer hardware 26 consists of "U" shaped upper guide members 28 and "U" shaped lower guide members 30 that are attached to the end of the sterilizer 12 on each side of the opening 13 to provide a system wherein the door 14 is free to slide vertically between an open position (See FIG. 1) and a closed position (See FIG. 2). A pulley and cable apparatus 40 utilizing a series of pulleys 42, 44, 46, and 48 and a cable 41 is adapted to move the door 14 between open and closed positions without interfering with the door retainer hardware 26.

Figure 4:
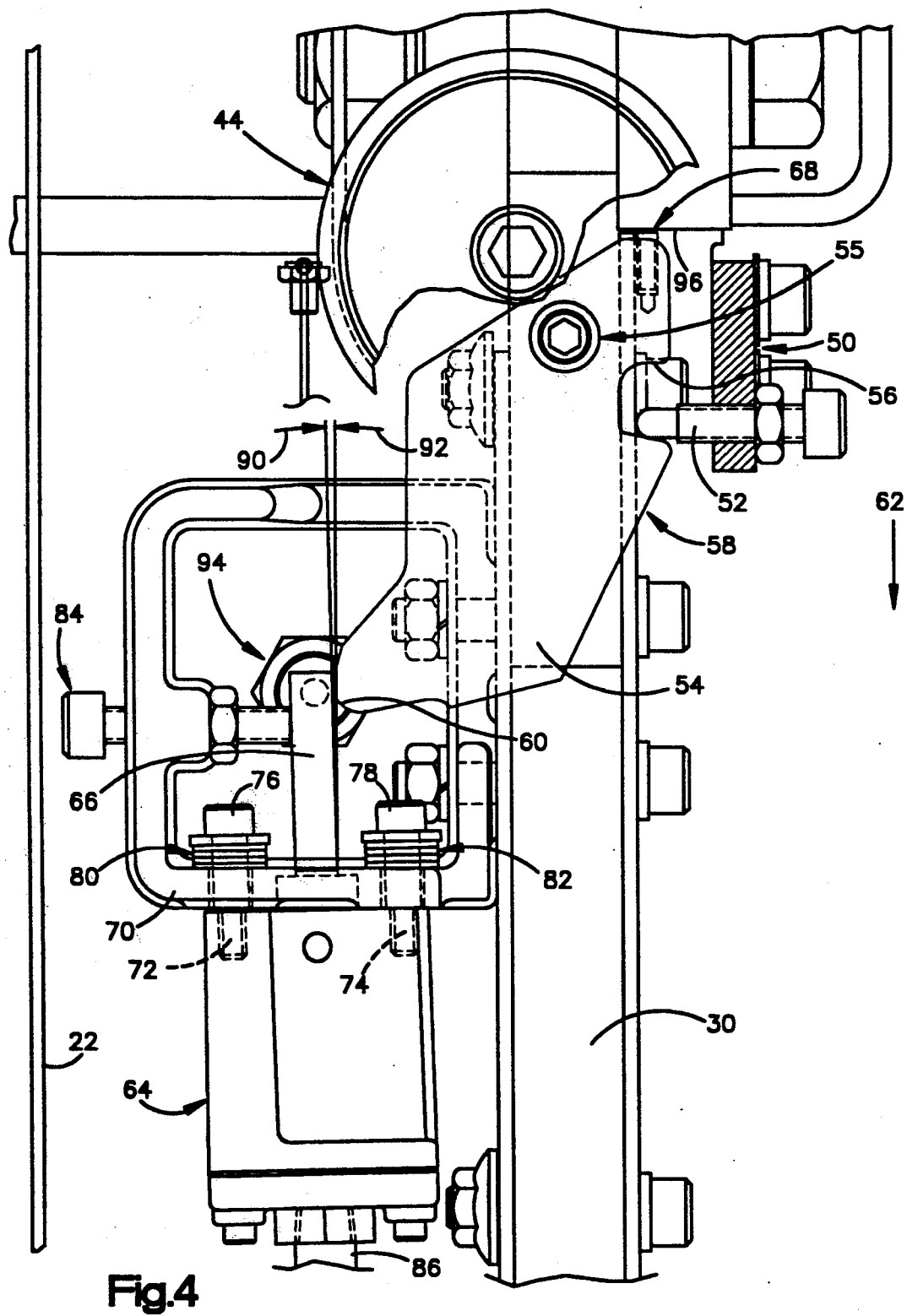
FIG. 4 is a side elevational view of the apparatus of the present invention with the door in the closed position.
Figure 7:
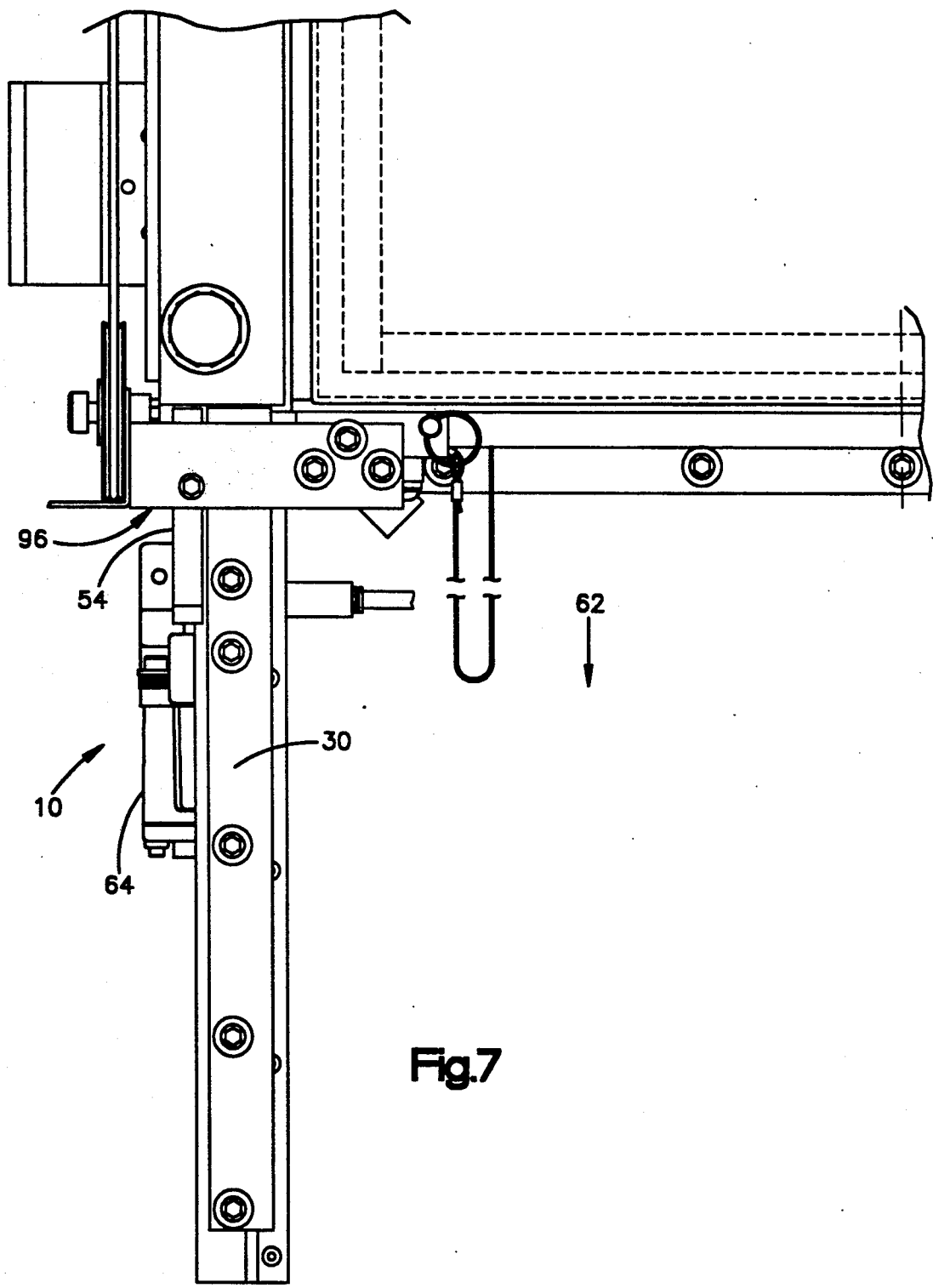
FIG. 7 is a front elevational view of the apparatus of the present invention.

The present invention is best seen in FIGS. 4-7. As shown in FIGS. 4 and 7, a door lift arm 50 is mounted to the door 14. A pin member 52 is mounted to the door lift arm 50 and is generally perpendicular to the door 14. A cam 54, pivotally mounted by shoulder bolt 55 to the guide member 30, cooperates with the pin 52 as will be described hereinbelow. It will be understood that other means of pivotal mounting may be utilized.

The cam 54 has a recessed area 56, a lobe surface 58 and a contact surface 60. As the door 14 moves in the direction of arrow 62, the cam is urged to rotate in the clockwise direction as shown by arrow 63 in FIG. 4.

Figure 5:
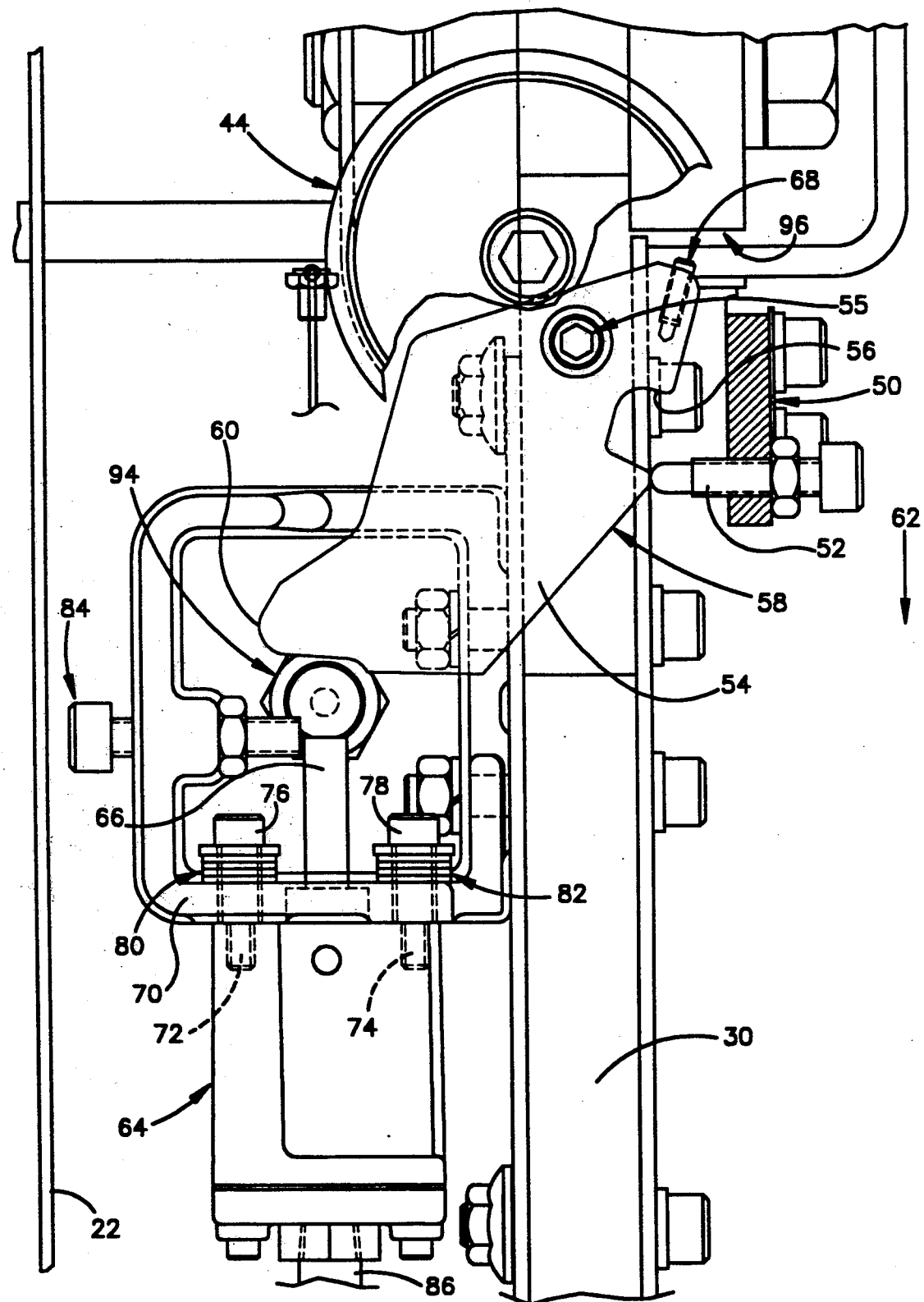
FIG. 5 is a side elevational view of the apparatus of the present invention with the door in the slightly open position and moving downward.
Figure 6:
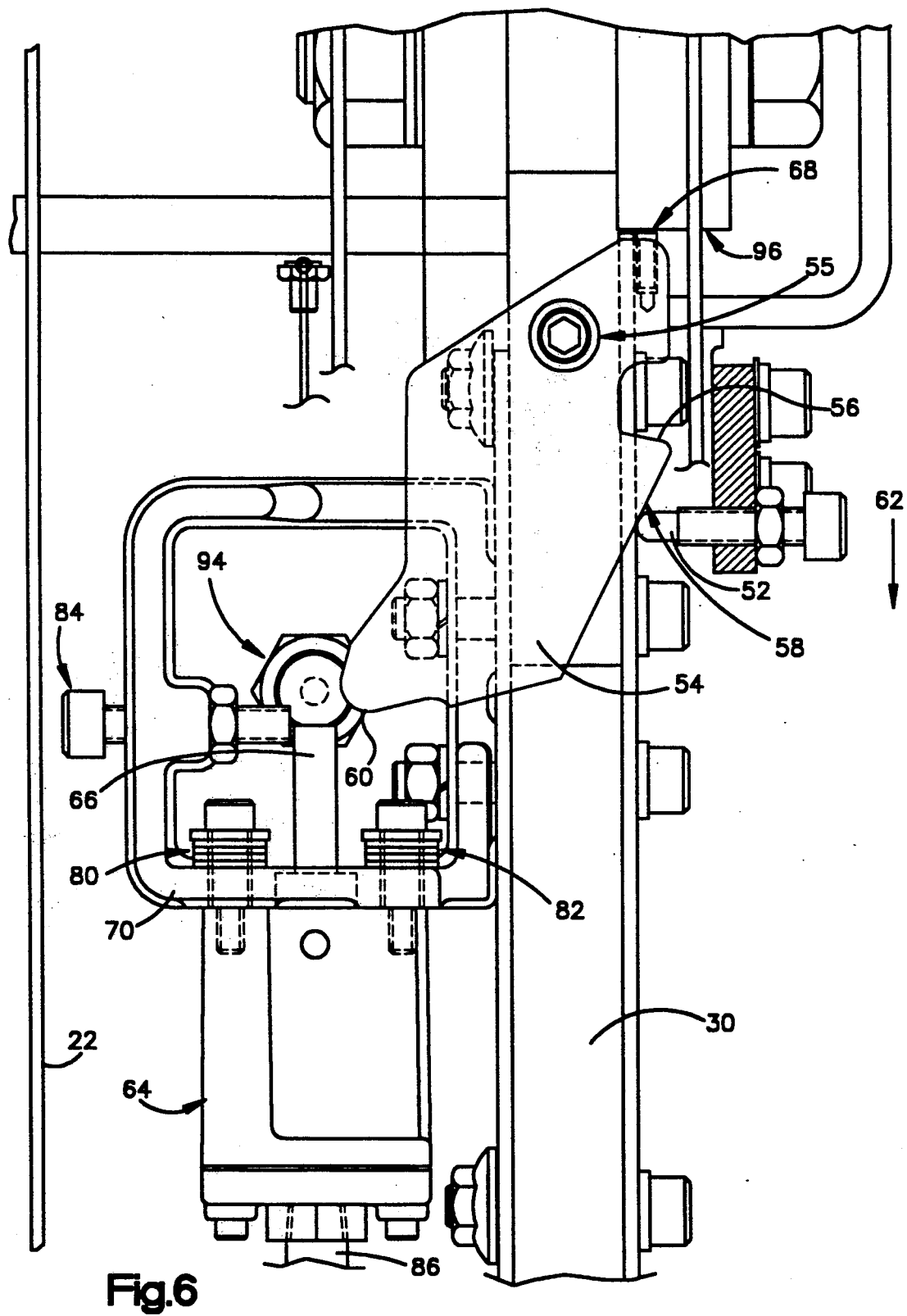
FIG. 6 is a side elevational view of the apparatus of the present invention with the door in the slightly open position and moving upward.

A cylinder 64 is mounted to the guide member 30 below the cam 54. A piston 66 of the cylinder 64 projects upward from the cylinder 64 and has two positions, an extended position, as shown in FIG. 4 and a retracted position, as shown in FIG. 5. When the piston 66 is in the extended position, the cam 54 cannot rotate and, thus, the pin 52 cannot move out of the recess 56. Accordingly, when the piston 66 is in the extended position, the pin 52 is blocked and the door 14 cannot open. When the piston 66 is retracted the cam 54 is free to rotate and the pin 52 may move past the recess 56 and along the lobe surface 58. Preferably, the cam 54 has its center of gravity below shoulder bolt 55 so that cam 54 is biased to its resting position as shown in FIG. 4, although other biasing means may be employed to ensure that cam 54 returns to its resting position shown in FIG. 4. Set screw 68 contacts the bottom surface 96 of the sterilizer 12 and may be adjusted to alter the resting position of cam 54.

The cylinder 64 is mounted to the guide member 30 in such a manner as to allow slight movement of the piston 66 and cylinder 64 when pin 52 causes the contact surface 60 to impinge on piston 66. A housing 70 is mounted to the guide member 30. The cylinder 64 is connected to the housing 70 by bolts 72 and 74 having heads 76 and 78, respectively. Between the heads 76 and 78 and the housing 70 are resilient washers 80 and 82, respectively. Alternatively, resilient washers 80 and 82 could be located between housing 70 and cylinder 64 below the housing 70 (not shown). This mounting allows for the cylinder 64 to rotate slightly since resilient washers 80 and 82 may deform in response to the force applied to the piston 66 by the contact surface 60. An adjustable stop pin 84 is mounted to the housing 70 and is perpendicular to the piston 66. The stop pin 84 may be adjusted to vary the distance that the piston 66 can move as indicated by the arcuate distance between arrows 90 and 92 in FIG. 4. Therefore, due to the flexible mounting of the cylinder 64, the piston 66 and cylinder 64 will not be damaged by the impact of the contact surface 60 of the cam 54.

The cylinder 64 is in fluid communication with the chamber 24 through line 86. When the chamber pressure is above a preselected minimum, for example 2 psi, the piston 66 extends and the door cannot be opened. The blocking apparatus, in the preferred embodiment, operates without any electrical components and, thus, is fail safe in the event of a power loss.

A proximity switch 94 can be utilized to electrically sense the location of the piston 66 to insure that the piston 66 is properly operating. The construction of electrical circuitry to receive feedback from the proximity switch 94 to determine the location of the piston is well within the skill of one of ordinary skill in the art.

It will be appreciated that various changes in the details, materials and arrangements of parts which have been herein described and illustrated in order to explain the nature of the invention, may be made by those skilled in the art within the principle and scope of the invention as expressed in the appended claims.

What is claimed is:

1. An apparatus for preventing the movement of a sliding door of a chamber from a closed position to an open position when the chamber pressure is above a preselected threshold, the chamber having an inside and an outside, comprising:
 a pin member attached to the door;
 a cam, pivotally attached to the outside of the chamber, said cam member having a recessed area, a lobe surface adjacent said recessed area and a contact surface;
 a piston having an extended position and a retracted position, said piston being in fluid communication with the chamber and being responsive to changes in chamber pressure above a preselected threshold such that said piston moves from said extended position to said retracted position when the chamber pressure falls below said preselected threshold;
 wherein said pin member, said cam and said piston are positioned relative to one another such that when the door is in the closed position and said piston is in said extended position said contact surface of said cam abuts said piston, said pin member is held captive by said recessed area, and movement of the door from the closed position to the open position is prevented, and when said piston is in said retracted position, the door moves said pin member along said lobe surface of said cam to rotate said cam thus allowing the door to move to the open position; and means for movably mounting said piston to said chamber such that said piston may move slightly in response to contact between said piston and said contact surface of said cam.

2. The apparatus recited in claim 1 wherein said means for movably mounting said cylinder to said chamber includes a housing for mounting said cylinder to the outside of the chamber, an adjustable stop screw mounted to said housing adjacent said piston for preselecting the degree of lateral movement of said piston, a fastener for mounting said cylinder to said chamber having a head portion and a resilient member between said head portion and said housing.

3. The apparatus recited in claim 1 wherein said cam has its center of gravity below the point of pivotal attachment.

4. The apparatus recited in claim 1 further including an adjustable set screw mounted on said cam, and wherein said sterilizer has a bottom surface, said set screw constructed to contact said bottom surface such that the position of said cam can be adjusted.

5. The apparatus recited in claim 1 further including a proximity switch adjacent said piston to electrically sense the position of said piston.

* * * * *